(12) United States Patent
Zheng (10) Patent No.: US 10,541,359 B2
(45) Date of Patent: Jan. 21, 2020

(54) SIMPLE-ASSEMBLY SENSING DEVICE

(71) Applicants: Interface Technology (ChengDu) Co., Ltd., Chengdu (CN); INTERFACE OPTOELECTRONICS (SHENZHEN) CO., LTD., Shenzhen (CN)

(72) Inventor: Xiao-Bing Zheng, Shenzhen (CN)

(73) Assignees: Interface Technology (ChengDu) Co., Ltd., Chengdu (CN); INTERFACE OPTOELECTRONICS (SHENZHEN) CO., LTD., Shenzhen (CN)

( * ) Notice: Subject to any disclaimer, the term of this patent is extended or adjusted under 35 U.S.C. 154(b) by 394 days.

(21) Appl. No.: 15/592,144

(22) Filed: May 10, 2017

(65) Prior Publication Data
US 2018/0204998 A1    Jul. 19, 2018

(30) Foreign Application Priority Data
Jan. 16, 2017   (CN) .......................... 2017 1 0032642

(51) Int. Cl.
  *H01L 41/08*  (2006.01)
  *B06B 1/06*   (2006.01)
  *G01N 29/24*  (2006.01)
(52) U.S. Cl.
  CPC ........ *H01L 41/0825* (2013.01); *B06B 1/0644* (2013.01); *G01N 29/2437* (2013.01); *G01N 2291/102* (2013.01)

(58) Field of Classification Search
  CPC ............ H01L 41/08; G01N 29/22; B06B 1/06
  See application file for complete search history.

(56) References Cited

U.S. PATENT DOCUMENTS

| 5,955,771 | A | * | 9/1999 | Kurtz | .................... G01L 19/147 257/419 |
| 6,058,782 | A | * | 5/2000 | Kurtz | .................... G01L 9/0042 73/727 |
| 2014/0060180 | A1 | * | 3/2014 | Lee | ........................ G01D 11/245 73/431 |

* cited by examiner

*Primary Examiner* — J. San Martin
(74) *Attorney, Agent, or Firm* — ScienBiziP, P.C.

(57) ABSTRACT

A solder-free sensing device includes a connecting assembly and a sensor. The connecting assembly includes a main body and at least two connecting pins engaged in the main body. The main body defines a receiving groove to receive the sensor. The sensor includes a first electrode layer and a second electrode layer insulated from the first electrode layer. Each connecting pin includes an end portion and an extending portion extending from the end portion. The end portion of each connecting pin is engaged in the receiving groove. The extending portion of each connecting pin extends through the main body to the outside of the main body. The sensor is electrically coupled to an external system by the at least two connecting pins.

19 Claims, 11 Drawing Sheets

SIMPLE-ASSEMBLY SENSING DEVICE

FIELD

The subject matter herein generally relates to a sensing device.

BACKGROUND

Sensing devices have been widely used in industrial, medical, and electronics fields. There are many different types of sensing devices, such as optical sensing devices, capacitive sensing devices, and ultrasonic wave sensing devices. However, electrodes of the sensing element of an ultrasonic sensing device are typically electrically coupled to an external system by connecting wires or a flexible printed circuit board, which requires a soldering process and labor costs for soldering. Therefore, there is room for improvement in the art.

BRIEF DESCRIPTION OF THE DRAWINGS

Implementations of the present technology will now be described, by way of example only, with reference to the attached figures.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "coupled" is defined as connected, whether directly or indirectly through intervening components, and is not necessarily limited to physical connections. The connection can be such that the objects are permanently connected or releasably connected. The term "comprising" when utilized, means "including, but not necessarily limited to"; it specifically indicates open-ended inclusion or membership in the so-described combination, group, series, and the like.

FIG. 1 through FIG. 4 illustrate a sensing device 100 according to an exemplary embodiment of the present application. The sensing device 100 includes a connecting assembly 1 and a sensor 2 mounted on the connecting assembly 1. The connecting assembly 1 is configured to receive the sensor 2 and electrically couple the sensor 2 to an external system (such as connecting device 8 described below). The external system can provide electrical power to the sensor 2 and transmit electrical signals from the sensor 2.

Figure 1:
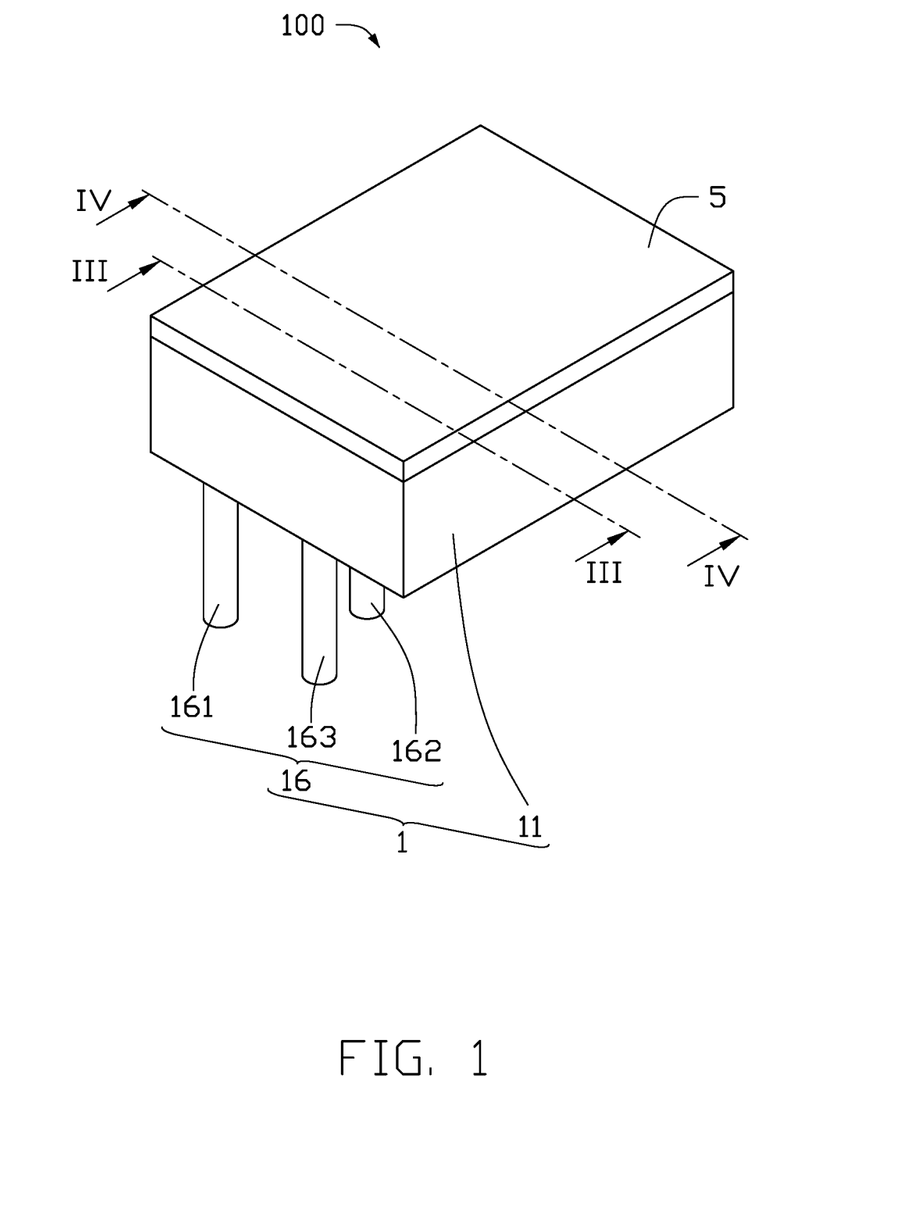
FIG. 1 is an isometric view of a first exemplary embodiment of a sensing device.
Figure 2:
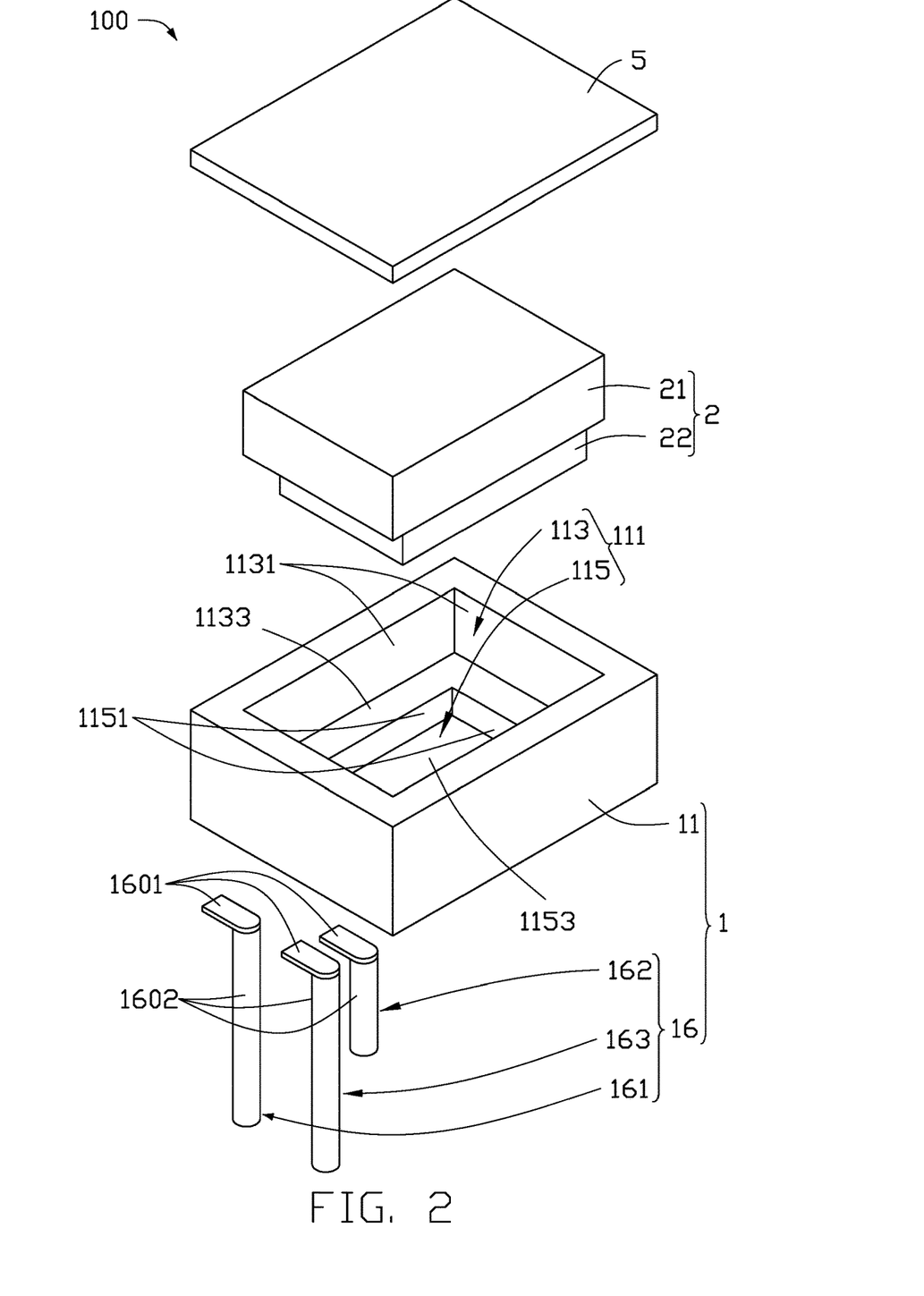
FIG. 2 is an exploded view of the sensing device of FIG. 1.

In the present exemplary embodiment, the sensor 2 is an ultrasonic sensor that is configured to send and receive ultrasonic waves and convert the received ultrasonic waves to electrical signals. As shown in FIG. 2, the sensor 2 includes a signal transmitting element 21 and a signal receiving element 22. In the present exemplary embodiment, the signal transmitting element 21 is stacked on the signal receiving element 22. The signal transmitting element 21 is configured to produce and transmit ultrasonic waves. The signal receiving element 22 is configured to receive ultrasonic waves. The signal transmitting element 21 has an area that is greater than an area of the signal receiving element 22, such that the signal receiving element 22 partially covers the signal transmitting element 21.

Figure 3:
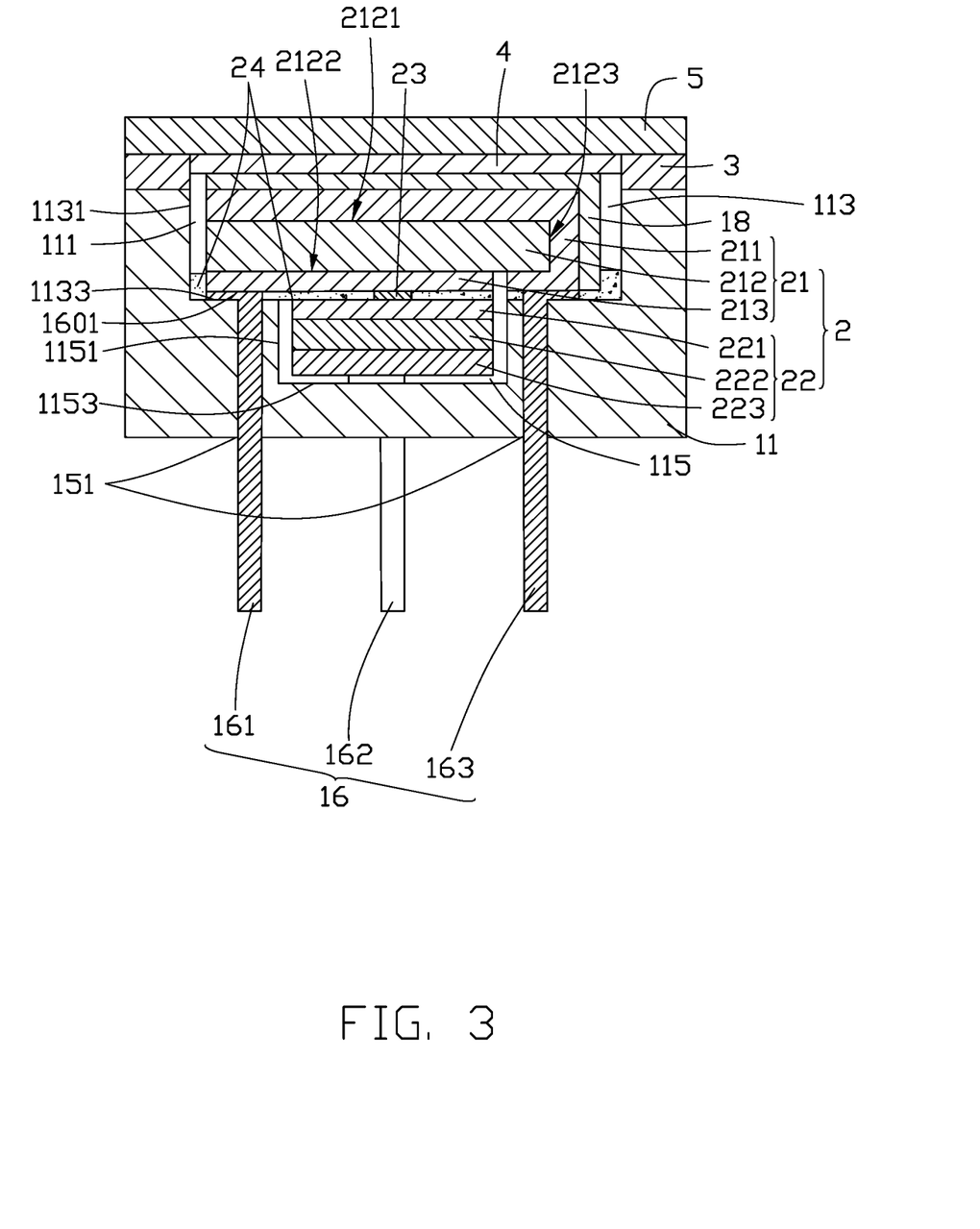
FIG. 3 is a cross-sectional view of the sensing device along line of FIG. 1.
Figure 4:
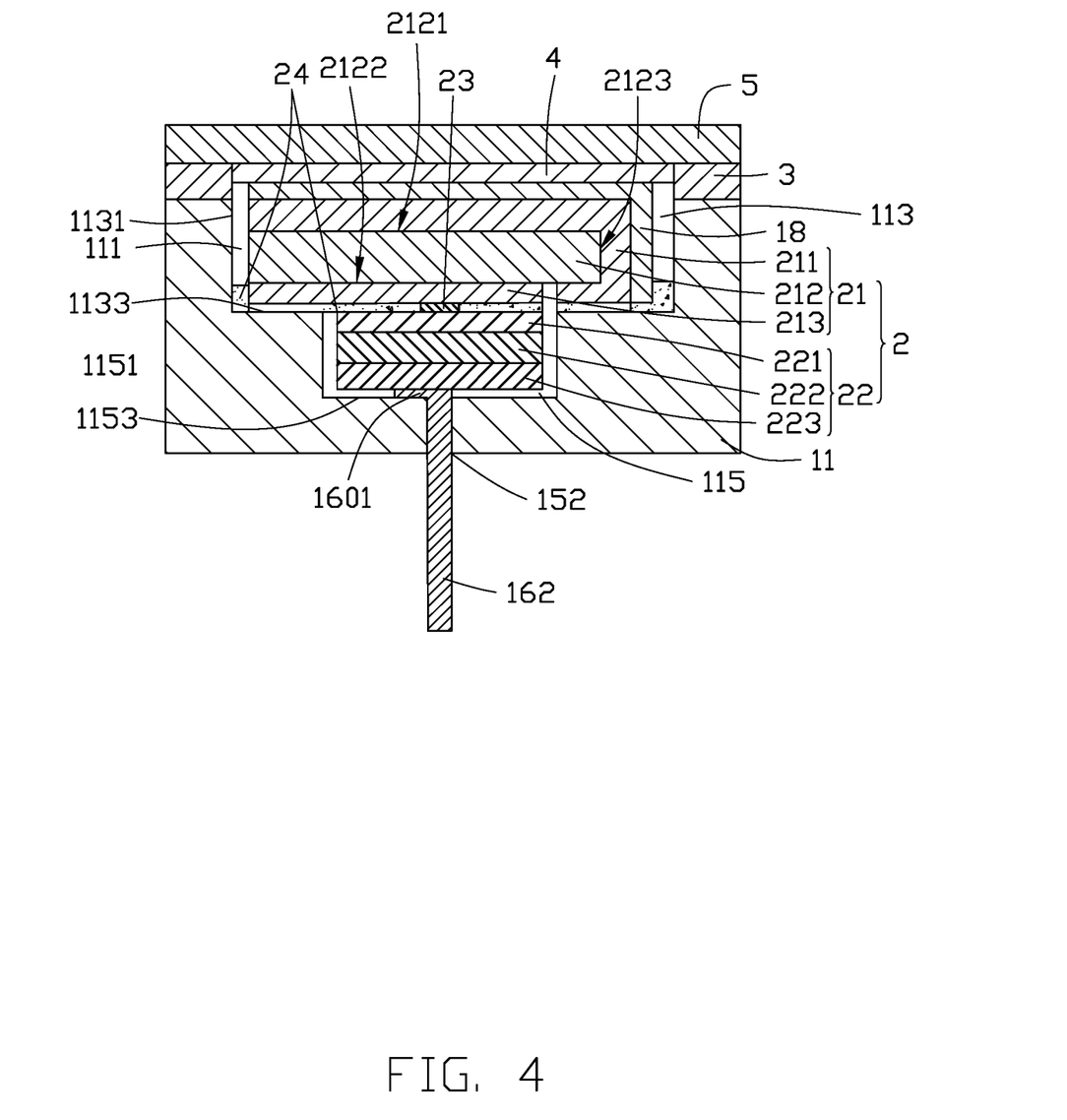
FIG. 4 is a cross-sectional view of the sensing device along line IV-IV of FIG. 1.

As shown in FIG. 3 and FIG. 4, the signal transmitting element 21 includes a first electrode layer 211, a second electrode layer 213, and a first piezoelectric material layer 212. The first electrode layer 211 and the second electrode layer 213 cooperatively form an electrical field. The first piezoelectric material layer 212 is capable of vibrating and producing ultrasonic waves under the electrical field. In the present embodiment, the first piezoelectric material layer 212 includes a first surface 2121 and a second surface 2122. The first surface 2121 and the second surface 2122 are on opposite sides facing away from each other. The first electrode layer 211 is formed on the first surface 2121 and covers the first surface 2121. The first electrode layer 211 extends to partially cover the second surface 2122. The second electrode layer 213 is formed on the second surface 2122, and partially covers the second surface 2122. The second electrode layer 213 is spaced apart from the first electrode layer 211. The first electrode layer 211 is electrically insulated from the second electrode layer 213.

As shown in FIG. 3 and FIG. 4, the first piezoelectric material layer 212 further includes a side surface 2123. The side surface 2123 is between and coupled to the first surface 2121 and the second surface 2122. The first electrode layer 211 covers the first surface 2121 and extends to cover the side surface 2123 and a portion of the second surface 2122.

In other embodiments, the first piezoelectric material layer 212 may define a through hole (not shown), and the first electrode layer 211 may extend through the first piezoelectric material layer 212 through the through hole to partially cover the second surface 2122.

As shown in FIG. 3 and FIG. 4, the signal receiving element 22 is attached to a side of the second electrode layer 213 facing away from the first piezoelectric material layer 212. The signal receiving element 22 includes a third electrode layer 221, a fourth electrode layer 223, and a second piezoelectric material layer 222 between the third electrode layer 221 and the fourth electrode layer 223. The third electrode layer 221 is attached to a side of the second electrode layer 213 facing away from the first piezoelectric material layer 212. The third electrode layer 221, the second piezoelectric material layer 222, and the fourth electrode layer 223 are stacked on the second electrode layer 213 in that order. A first binder layer 24 is formed between the second electrode layer 213 and the third electrode layer 221. Thus, the signal receiving element 22 and the signal transmitting element 21 are coupled together. The second electrode layer 213 is electrically coupled to the third electrode layer 221 by an electrically conductive portion 23, which gives the second electrode layer 213 and the third electrode layer 221 the same electrical potential. The third electrode layer 221 is electrically insulated from the fourth electrode layer 223.

In the present exemplary embodiment, the first binder layer 24 is electrically insulating. The electrically conductive portion 23 is embedded into the first binder layer 24 and extends through the first binder layer 24 to couple between the second electrode layer 213 and the third electrode layer 221. The electrically conductive portion 23 can include electrically conductive material, such as anisotropic conductive adhesive, and adhesive containing silver particles.

Figure 5:
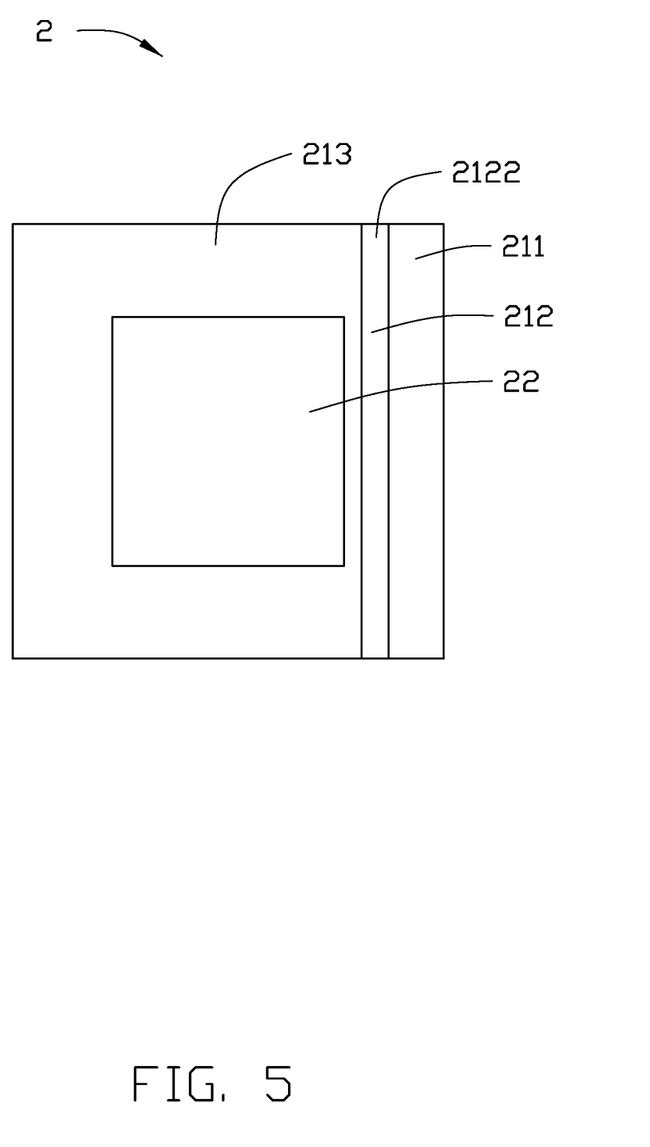
FIG. 5 is a bottom view of a first exemplary embodiment of a sensor of the sensing device of FIG. 2.

Both the first electrode layer 211 and the second electrode layer 213 partially cover the second surface 2122 of the first piezoelectric material layer 212. As shown in FIG. 5, in one embodiment, the first electrode layer 211 covers an edge portion of the second surface 2122. An uncovered portion of the second surface 2122 is positioned between the first electrode layer 211 and the second electrode layer 213. The uncovered portion of the second surface 2122 has a strip shape. The signal receiving element 22 is stacked on the second electrode layer 213 and partially covers the second electrode layer 213.

Figure 6:
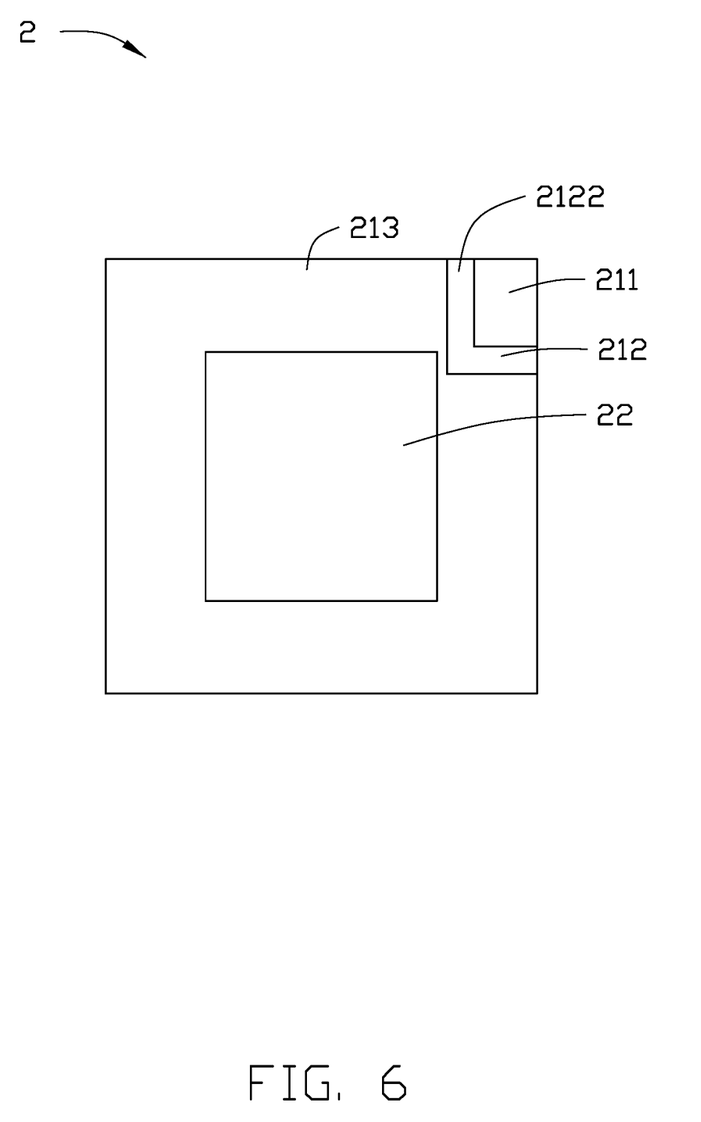
FIG. 6 is a bottom view of a second exemplary embodiment of a sensor of the sensing device of FIG. 2.

As shown in FIG. 6, in another embodiment, the first electrode layer 211 extends to partially cover a corner portion of the second surface 2122 of the first piezoelectric material layer 212. The uncovered portion of the second surface 2122 is substantially an "L" shape. The signal receiving element 22 is stacked on the second electrode layer 213 and partially covers the second electrode layer 213. It is noted that certain elements of the sensing device 100 are omitted from or rendered transparent in FIGS. 5 and 6 for visual clarity, which would otherwise be present as parts of the sensing devices.

The first electrode layer 211, the second electrode layer 213, the third electrode layer 221, and the fourth electrode layer 223 are made of electrically conductive material, such as silver, copper, molybdenum, or indium tin oxide. Both the first piezoelectric material layer 212 and the second piezoelectric material layer 222 are made of a piezoelectric material, such as polyvinylidene fluoride and lead zirconate titanate piezoelectric ceramic.

As shown in FIG. 2, the connecting assembly 1 includes a main body 11 and at least two connecting pins 16 engaged in the main body 11. The main body 11 is configured to receive the sensor 2. The at least two connecting pins 16 are configured to electrically couple the sensor 2 to a connecting device 6 (described below with reference to FIG. 8). The main body 11 is made of electrically insulative material, such as polycarbonate or polymethylmethacrylate. Each connecting pin 16 is made of electrically conductive material, such as silver, copper, molybdenum, or indium tin oxide.

The main body 11 defines a receiving groove 111 to receive the sensor 2. The receiving groove 111 matches the sensor 2 and includes a first portion 113 and a second portion 115 air communicating with the first portion 113. The first portion 113 has a size that is greater than a size of the second portion 115. The signal transmitting element 21 is received in the first portion 113; and the signal receiving element 22 is received in the second portion 115.

The first portion 113 of the receiving groove 111 includes at least one first side wall 1131 and a first bottom wall 1133 connecting to the at least one first side wall 1131. In the present exemplary embodiment, as shown in FIG. 2, there are four first side walls 1131. The second portion 115 of the receiving groove 111 includes at least one second side wall 1151 and a second bottom wall 1153 connecting to the at least one second side wall 1151. In the present exemplary embodiment, as shown in FIG. 2, there are four second side walls 1151. The first bottom wall 1133 is connected between the at least one first side wall 1131 and the at least one second side wall 1151. The second portion 115 extends through the first bottom wall 1133 to air communicate with the first portion 113. As shown in FIG. 3 and FIG. 4, when the sensor 2 is received in the receiving groove 111 of the main body 11, the first electrode layer 211 and the second electrode layer 213 are stacked on the first bottom wall 1133, while the fourth electrode layer 223 is stacked on the second bottom wall 1153.

Figure 7:
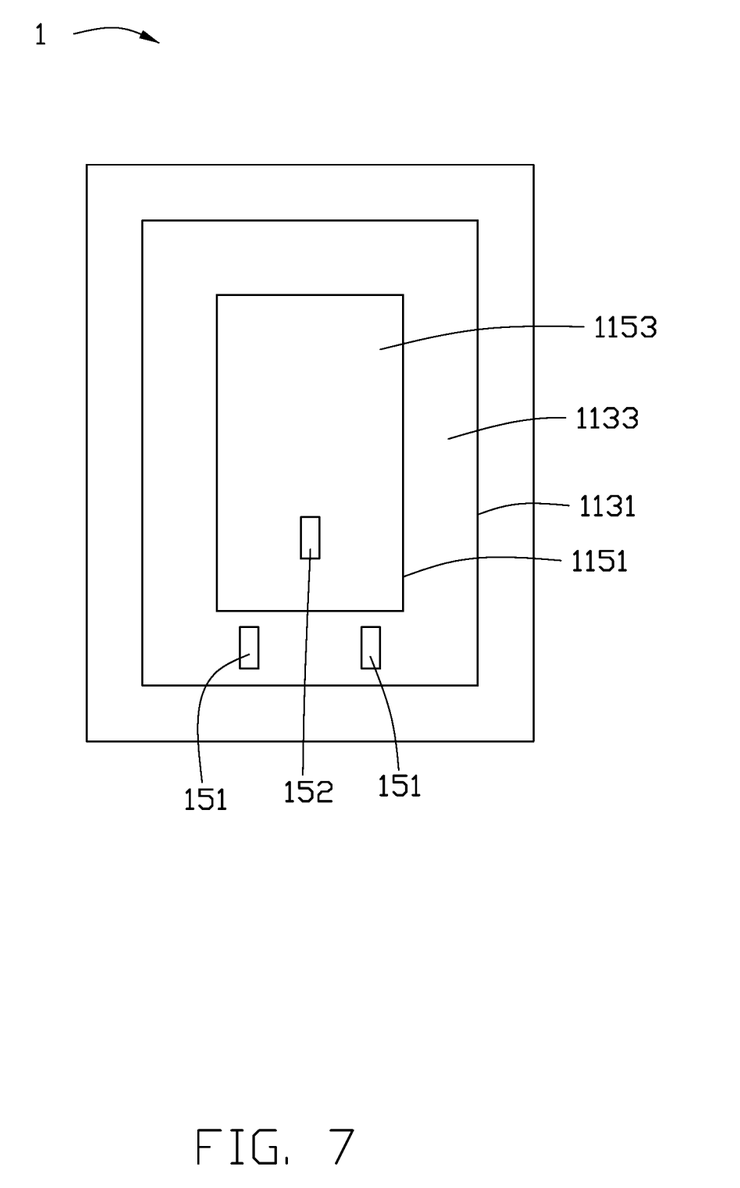
FIG. 7 is a plan view of an exemplary embodiment of a connecting assembly of the sensing device of FIG. 2.

As shown in FIG. 3 and FIG. 7, the first bottom wall 1133 defines two first through holes 151. Each of the two first through holes 151 extends through the main body 11. As shown in FIG. 4 and FIG. 7, the second bottom wall 1153 defines a second through hole 152. The second through hole 152 extends through the main body 11.

As shown in FIG. 2, each connecting pin 16 includes an end portion 1601 and an extending portion 1602 extending from the end portion 1601. In the present exemplary embodiment, the extending portion 1602 substantially perpendicularly extends from the end portion 1601. In the present exemplary embodiment, there are three connecting pins 16, which are defined as a first connecting pin 161, a second connecting pin 162, and a third connecting pin 163. The extending portion 1602 of each connecting pin 16 extends into the first through hole 151 or the second through hole 152 to the outside of the main body 11. The end portion 1601 of each connecting pin 16 has a size that is greater than a size of the first through hole 151 or the second through hole 152. As such the end portion 1601 of each connecting pin 16 is positioned outside of the first through hole 151 and the second through hole 152, and no connecting pin 16 can slide out of the main body 11 through the first through hole 151 or the second through hole 152.

As shown in FIG. 3, the end portion 1601 of the first connecting pin 161 is received in the receiving groove 111 and directly contacts the second electrode layer 213. The end portion 1601 of the second connecting pin 162 is received in the receiving groove 111 and directly contacts the first electrode layer 211. As shown in FIG. 4, the end portion 1601 of the third connecting pin 162 is received in the receiving groove 111 and directly contacts the fourth electrode layer 223.

In the present exemplary embodiment, the first connecting pin 161 and the third connecting pin 163 may have a same length. The second connecting pin 162 may have a length that is less than the length of the third connecting pin 163.

As shown in FIG. 2 through FIG. 5, the sensing device 100 further includes a cover 5. The cover 5 covers the connecting assembly 1, and especially covers the receiving groove 111 of the connecting assembly 1. The sensor 2 is thus enclosed by the connecting assembly 1 and the cover 5. The cover 5 can be made of stainless steel, glass, or plastic.

A second binder layer 3 is formed between the cover 5 and the main body 11. As such, the cover 5 and the connecting assembly 1 are bonded together. A third binder layer 4 is formed between the cover 5 and the sensor 2. As such, the cover 5 and the sensor 2 are bonded together. The second binder layer 3 is a conventional binder. The third binder layer 4 is a binder which can be cured at room temperature and is rendered hard by curing. The third binder layer 4 can effectively reduce any decaying of the ultrasonic waves when the ultrasonic waves pass through the third binder layer 4. The thickness of the third binder layer 4 is less than 100 μm. In one exemplary embodiment, the thickness of the third binder layer 4 is less than 20 μm.

In the present exemplary embodiment, as shown in FIG. 3 and FIG. 4, a protecting layer 18 is formed on the first electrode layer 211 to protect the first electrode layer 211. For example, the protecting layer 18 may be made of polytetrafluoroethylene.

Figure 8:
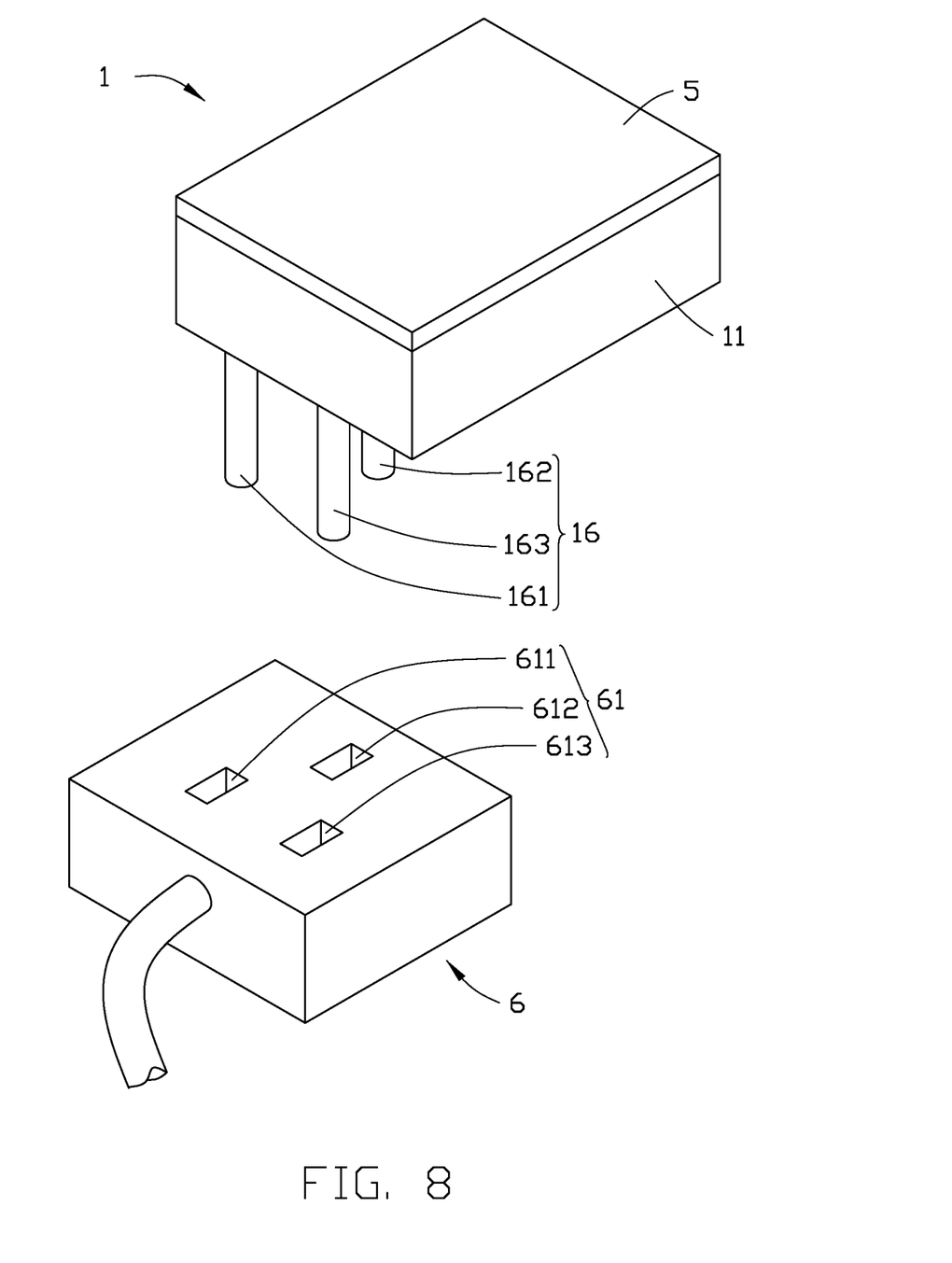
FIG. 8 is an isometric view of an exemplary embodiment of a connecting device coupled to the connecting assembly of FIG. 7.

The sensing device 100 can be electrically coupled to a connecting device 6 as shown in FIG. 8. The connecting device 6 defines three connecting terminals 61, which are defined as a first connecting terminal 611, a second connecting terminal 612, and a third connecting terminal 613. The first connecting pin 161 is inserted into the first connecting terminal 611, the second connecting pin 162 is inserted into the second connecting terminal 612, and the third connecting pin 163 is inserted into the third connecting terminal 613. As such, the sensing device 100 is electrically coupled to the connecting device 6. The connecting device 6 may provide electrical power to the sensor 2 and receive the electrical signals from the sensor 2.

In use, an object to be investigated (object, such as a finger, not shown) is touching on the cover 5, and an electric field (not shown) is formed between the first electrode layer 211 and the second electrode layer 213. The first piezoelectric material layer 212 vibrates and produces ultrasonic waves under the electric field. The ultrasonic waves pass through the cover 5 and reach the object to be investigated. The object to be investigated reflects the ultrasonic waves back to the signal receiving element 22, and the signal receiving element 22 receives the reflected ultrasonic signals and converts the reflected ultrasonic signals into electrical signals. The electrical signals may be transmitted to the connecting device 6 by the second connecting pin 162.

Figure 9:
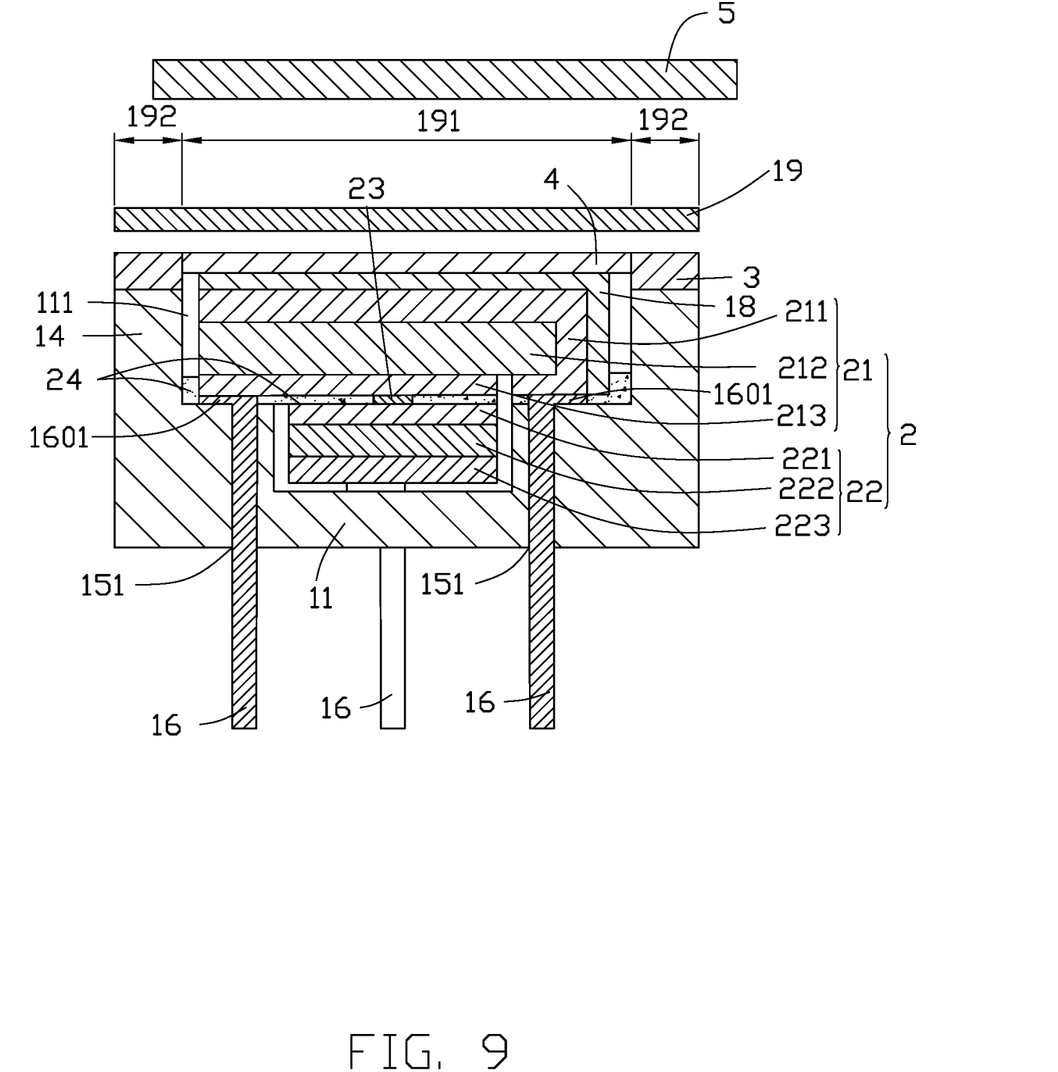
FIG. 9 is a cross-sectional view of the sensing device of FIG. 2 during an assembling process.

In assembly, the extending portion 1602 of each connecting pin 16 is inserted into the first through hole 151 or the second through hole 152 as shown in FIG. 3 and FIG. 4, and the end portion 1601 of each connecting pin 16 is received in the receiving groove 111 of the main body 11. As shown in FIG. 9, a second binder layer 3 is coated on a surface of the main body 11 facing the cover 5. Then the sensor 2 with a release film 19 covering the first electrode layer 211 is positioned in the receiving groove 111 of the main body 11. A first portion 191 of the release film 19 corresponding to the receiving groove 111 is removed from the sensor 2, other portion 192 of the release film 19 remains on the sensor 2. A third binder layer 4 is coated on the sensor 2 that is received in the receiving groove 111. Next, the other portion 192 of the release film 19 is removed. Finally, the cover 5 is bonded to the connecting assembly 1 and the sensor 2 by the second binder layer 3 and the third binder layer 4.

Figure 10:
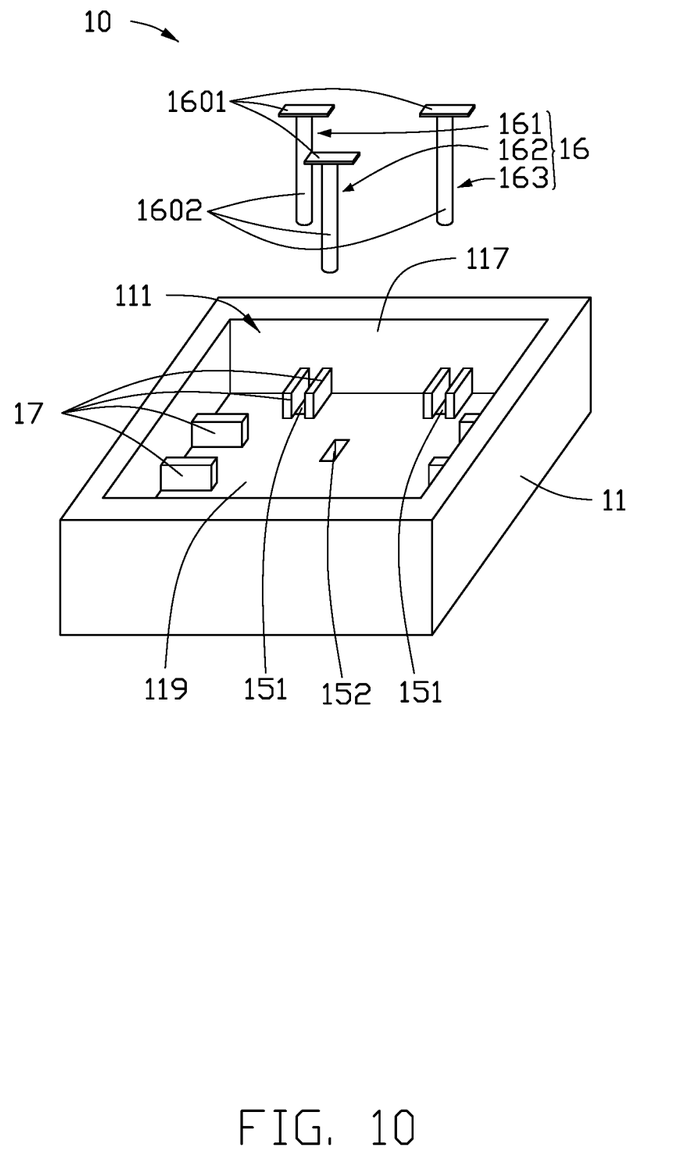
FIG. 10 is an exploded view of a second exemplary embodiment of a connecting assembly.

FIG. 10 illustrates a connecting assembly 10 according to a second exemplary embodiment. The connecting assembly 10 can substitute the connecting assembly 1 as described above to receive the sensor 2. The connecting assembly 10 includes a main body 11 and at least two connecting pins 16. The main body 11 is configured to receive the sensor 2. The at least two connecting pins 16 are configured to electrically couple the sensor 2 to the connecting device 6. The main body 11 is made of an electrically insulative material, such as polycarbonate or polymethylmethacrylate. Each connecting pin 16 is made of electrically conductive material, such as silver, copper, molybdenum, or indium tin oxide.

As shown in FIG. 10, the main body 11 defines a receiving groove 111 to receive the sensor 2. The receiving groove 111 includes at least one side wall 117 and a bottom wall 119 connecting to the at least one side wall 117. In the present exemplary embodiment, there are four side walls 117. The main body 11 includes a plurality of supporting portions 17 protruding from the bottom wall 119. The plurality of supporting portions 17 is configured to support the sensor 2, especially supporting the signal transmitting element 21 of the sensor 2. When the sensor 2 is received in the receiving groove 111 of the main body 11, the first electrode layer 211 and the second electrode layer 213 are stacked on the plurality of supporting portion 17. The fourth electrode layer 223 is stacked on the bottom wall 119.

As shown in FIG. 10, the bottom wall 119 defines two first through holes 151 and a second through hole 152. Each of the two first through holes 151 extends through the main body 11. The second through hole 152 extends through the main body 11. Each of the two first through hole 151 is located between two adjacent supporting portions 17.

Each connecting pin 16 includes an end portion 1601 and an extending portion 1602 extending from the end portion 1601. In the present exemplary embodiment, the extending portion 1602 substantially perpendicularly extends from the end portion 1601. In the present exemplary embodiment, there are three connecting pins 16, defined as a first connecting pin 161, a second connecting pin 162, and a third connecting pin 163. The end portion 1601 of each connecting pin 16 has a size that is greater than a size of the first through hole 151 or the second through hole 152. As such, the end portion 1601 of each connecting pin 16 is positioned outside of the first through hole 151 and the second through hole 152, and no connecting pin 16 can slide out of the main body 11 through the first through hole 151 or the second through hole 152.

The extending portion 1602 of the first connecting pin 161 extends into one of the two first through holes 151 to the outside of the main body 11. The end portion 1601 of the first connecting pin 161 is received in the receiving groove 111 and supported by the two adjacent supporting portions 17 corresponding to the first through holes 151. Thus, the end portion 1601 of the first connecting pin 161 can directly contact the first electrode layer 211 of the sensor 2. The extending portion 1602 of the third connecting pin 163 extends into another first through hole 151 to the outside of the main body 11; and the end portion 1601 of the third connecting pin 163 is received in the receiving groove 111 and supported by the two adjacent supporting portions 17 corresponding to the first through holes 151. Thus, the end portion 1601 of the third connecting pin 163 can directly contact the second electrode layer 213 of the sensor 2.

The extending portion 1602 of the second connecting pin 162 extends into the second through hole 152 to the outside of the main body 11; and the end portion 1601 of the second connecting pin 162 is received in the receiving groove 111 and supported by the bottom wall 119. Thus, the end portion 1601 of the second connecting pin 162 can directly contact the fourth electrode layer 223 of the sensor 2.

Figure 11:
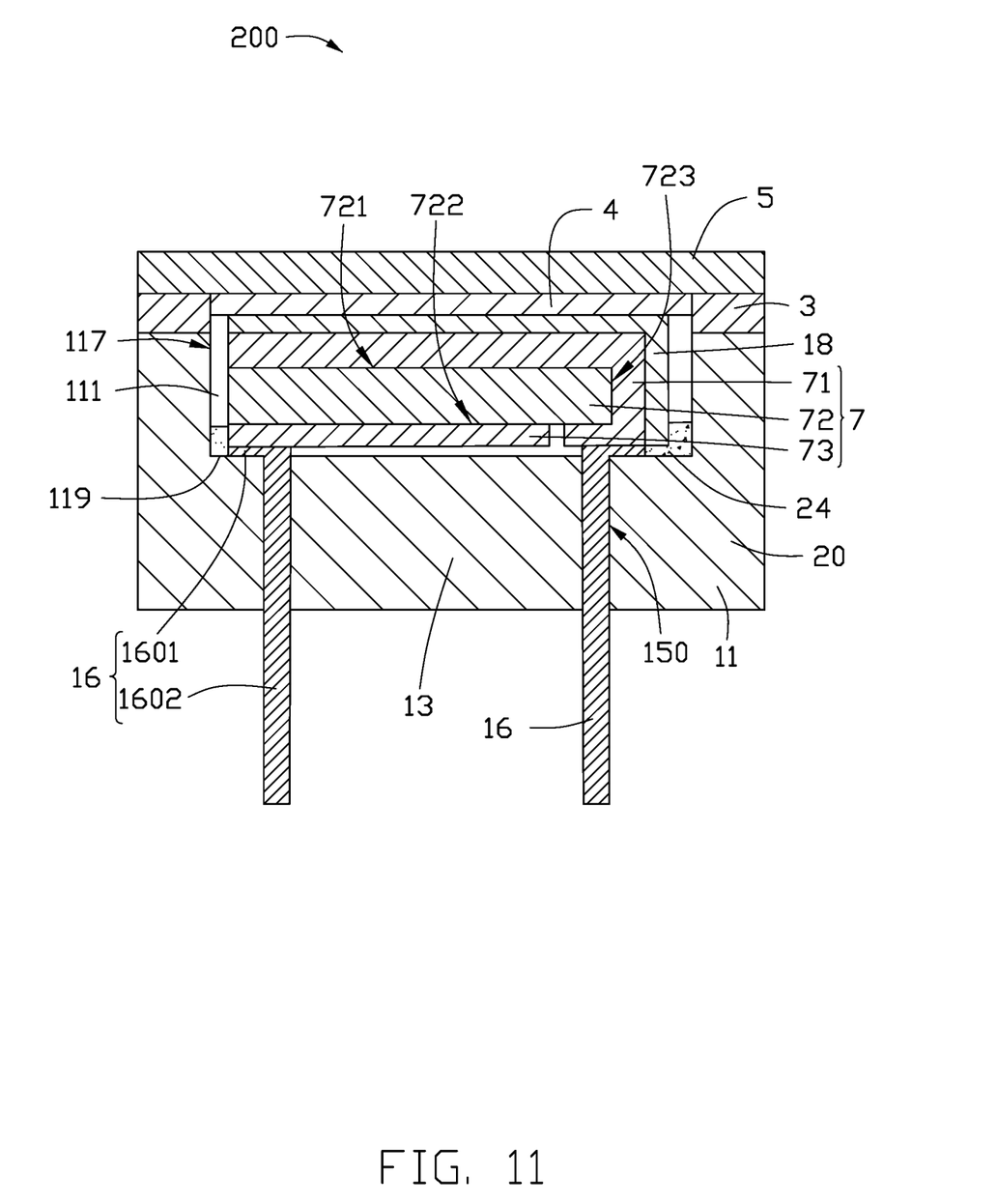
FIG. 11 is a cross-sectional view of a second exemplary embodiment of a sensing device.

FIG. 11 illustrates a sensing device 200 according to a second exemplary embodiment. The sensing device 200 includes a connecting assembly 20 and a sensor 7 mounted on the connecting assembly 20. The connecting assembly 20 is configured to receive the sensor 7 and electrically couple the sensor 7 to an external system (not shown). The external system may provide electrical power to the sensor 7 and receive the electrical signals from the sensor 7.

The sensor 7 is a capacitive sensor. As shown in FIG. 11, the sensor 7 includes a first electrode layer 71, a second electrode layer 73, and an insulating layer 72. The insulating layer 72 is elastic. When an object (not shown) is touching the sensor 7, the insulating layer 72 deforms, and distance between the first electrode layer 71 and the second electrode layer 73 decreases, thus capacitance between the first electrode layer 71 and the second electrode layer 73 is modified. Both the first electrode layer 71 and the second electrode layer 73 are made of an electrically-conductive material, such as silver, copper, molybdenum, or indium tin oxide.

In the present exemplary embodiment, the insulating layer 72 includes a first surface 721 and a second surface 722. The first surface 721 and the second surface 722 are on opposite sides facing away from each other. The first electrode layer 71 covers the first surface 721 and extends to partially cover the second surface 722. The second electrode layer 73 partially covers the second surface 722 and is spaced apart from the first electrode layer 71. The second electrode layer 73 is electrically insulated from the first electrode layer 71.

As shown in FIG. 11, the insulating layer 72 further includes a side surface 723. The side surface 723 is coupled between the first surface 721 and the second surface 722. The first electrode layer 71 covers the first surface 721 and extends to cover the side surface 723 and the second surface 722. In other embodiments, the insulating layer 72 may define a through hole (not shown), and the first electrode layer 71 may extend through the insulating layer 72 through the through hole to partially cover the second surface 722.

The connecting assembly 20 includes a main body 11 and two connecting pins 16. The two connecting pins 16 are configured to electrically couple the sensor 7 to a connecting device (not shown). The main body 11 is made of an electrically insulative material, such as polycarbonate or polymethylmethacrylate. Each connecting pin 16 is made of electrically conductive material, such as silver, copper, molybdenum, or indium tin oxide.

As shown in FIG. 11, the main body 11 defines a receiving groove 111 to receive the sensor 7. The receiving groove 111 includes at least one side wall 117 and a bottom wall 119 connecting to the at least one side wall 117. When the sensor 7 is received in the receiving groove 111 of the main body 11, the first electrode layer 71 and the second electrode layer 73 are stacked on the bottom wall 119. The bottom wall 119 defines two through holes 150. Each through hole 150 extends through the main body 11.

Each connecting pin 16 includes an end portion 1601 and an extending portion 1602 extending from the end portion 1601. In the present exemplary embodiment, the extending portion 1602 substantially perpendicularly extends from the end portion 1601. The end portion 1601 of each connecting pin 16 has a size that is greater than a size of each of the through hole 150. As such the end portion 1601 of each connecting pin 16 is positioned outside of the through hole 150, and no connecting pin 16 can slide out of the main body 11 through the through hole 150.

The extending portion 1602 of each connecting pin 16 extends into one of the two through holes 150 to the outside of the main body 11. The end portion 1601 of each connecting pin 16 is received in the receiving groove 111 and supported by the bottom wall 119. Thus, the end portion 1601 of one connecting pin 16 can directly contact the first electrode layer 71 of the sensor 7, and the end portion 1601 of another connecting pin 16 can directly contact the second electrode layer 73 of the sensor 7.

The sensing device 200 further includes a cover 5. The cover 5 covers the connecting assembly 20, and especially covers the receiving groove 111 of the main body 11. As such the sensor 7 is enclosed by the connecting assembly 20 and the cover 5. The cover 5 can be made of stainless steel, glass, or plastic.

A binder layer 3 is formed between the cover 5 and the main body 11, the cover 5 and the main body 11 are thereby bonded together. A binder layer 4 is formed between the cover 5 and the sensor 7, the cover 5 and the sensor 7 are thereby bonded together. The binder layer 3 is a conventional binder. The third binder layer 4 is a binder which can be cured at room temperature and becomes hard on curing. The third binder layer 4 can effectively reduce any decaying of the ultrasonic waves when the ultrasonic waves passes through the third binder layer 4. The thickness of the binder layer 4 is less than 100 μm. In one exemplary embodiment, the thickness of the binder layer 4 is less than 20 μm. In the present exemplary embodiment, as shown in FIG. 11, a protecting layer 18 is formed on the first electrode layer 71 to protect the first electrode layer 71. For example, the protecting layer 18 may be of polytetrafluoroethylene.

It is to be understood, even though information and advantages of the present exemplary embodiments have been set forth in the foregoing description, together with details of the structures and functions of the present exemplary embodiments, the disclosure is illustrative only. Changes may be made in detail, especially in matters of shape, size, and arrangement of parts within the principles of the present exemplary embodiments to the full extent indicated by the plain meaning of the terms in which the appended claims are expressed.

What is claimed is:

1. A sensing device comprising:
   a connecting assembly, the connecting assembly comprising a main body and at least two connecting pins engaged in the main body, the main body defining a receiving groove;
   a sensor, the sensor received in the receiving groove and comprising a first electrode layer and a second electrode layer insulated from the first electrode layer, the first electrode layer extending to locate at a same plane with the second electrode layer;
   wherein each of the at least two connecting pins is made of electrically conductive material; each of the at least two connecting pins comprises an end portion and an extending portion extending from the end portion; the end portion of each of the at least two connecting pins is engaged in the receiving groove, the extending portion of each of the at least two connecting pins extends through the main body to the outside of the main body; and
   wherein the first electrode layer is in direct contact with the end portion of one of the at least two connecting pins and the second electrode layer is in direct contact with the end portion of another one of the at least two connecting pins, the sensor is electrically coupled to an external system by the at least two connecting pins;

wherein the sensor is an ultrasonic sensor, the sensor comprises a signal transmitting element and a signal receiving element stacked on the signal transmitting element the signal transmitting element is configured to produce and transmit ultrasonic waves; the signal receiving element is configured to receive ultrasonic waves; and the signal transmitting element comprises the first electrode layer, the second electrode layer, and a first piezoelectric material layer between the first electrode layer and the second electrode layer.

2. The sensing device of claim 1, wherein the main body is made of an electrically insulative material.

3. The sensing device of claim 1, wherein the first piezoelectric material layer comprises a first surface and a second surface; the first surface and the second surface are on opposite sides facing away from each other; the first electrode layer is formed on the first surface and covers the first surface; the first electrode layer extends to partially cover the second surface; the second electrode layer is formed on the second surface and partially covers the second surface.

4. The sensing device of claim 3, wherein the first piezoelectric material layer further comprises a side surface coupled between the first surface and the second surface; the first electrode layer extends to cover the side surface and the second surface.

5. The sensing device of claim 1, wherein the signal receiving element comprises a third electrode layer formed on a side of the second electrode layer facing away from the first piezoelectric material layer, a fourth electrode layer stacked on the third electrode layer, and a second piezoelectric material layer between the third electrode layer and the fourth electrode layer.

6. The sensing device of claim 5, wherein the second electrode layer is electrically coupled to the third electrode layer by an electrically conductive portion.

7. The sensing device of claim 6, wherein a first binder layer is formed between the second electrode layer and the third electrode layer, the first binder layer is electrically insulating, the electrically conductive portion is embedded into the first binder layer and extends through the first binder layer to couple between the second electrode layer and the third electrode layer.

8. The sensing device of claim 1, wherein the signal transmitting element has an area that is greater than an area of the signal receiving element; the signal receiving element partially covers the signal transmitting element.

9. The sensing device of claim 8, wherein the receiving groove matches the sensor and comprises a first portion and a second portion air communicating with the first portion; the first portion has a size that is greater than a size of the second portion; the signal transmitting element is received in the first portion; and the signal receiving element is received in the second portion.

10. The sensing device of claim 9, wherein the first portion of the receiving groove comprises at least one first side wall and a first bottom wall connecting to the at least one first side wall; the second portion of the receiving groove comprises at least one second side wall and a second bottom wall connecting to the at least one second side wall; the first bottom wall is connected between the at least one first side walls and the at least one second side wall; the first electrode layer and the second electrode layer are stacked on the first bottom wall; the first bottom wall defines two first through holes extending through the main body; the at least two connecting pins comprises a first connecting pin and a second connecting pin, the extending portion of the first connecting pin or the second connecting pin extends into one of the two first through hole to the outside of the main body.

11. The sensing device of claim 10, wherein the at least two connecting pins further comprises a third connecting pin; the second bottom wall defines a second through hole; the extending portion of the third connecting pin extends into the second through hole to the outside of the main body; the signal receiving element is stacked on the second bottom wall; the signal receiving element is in direct contact with the end portion of the third connecting pin.

12. The sensing device of claim 10, wherein the end portion of each of the at least two connecting pins has a size that is greater than a size of each of the two first through holes.

13. The sensing device of claim 8, wherein the receiving groove comprises at least one side wall and a bottom wall connecting to the at least one side wall; the main body comprises a plurality of supporting portion protruding from the bottom wall; the plurality of supporting portion is configured to support the signal transmitting element.

14. The sensing device of claim 13, wherein the first electrode layer and the second electrode layer are stacked on the plurality of supporting portion; and the signal receiving element is stacked on the bottom wall.

15. The sensing device of claim 14, wherein the bottom wall defines two first through holes; each of the two first through holes extends through the main body; each of the two first through hole is located between two adjacent supporting portions; the at least two connecting pins comprises a first connecting pin and a second connecting pin, the extending portion of the first connecting pin or the second connecting pin extends into one of the two first through hole to the outside of the main body; the end portion of the first connecting pin or the second connecting pin is supported by the two adjacent supporting portions.

16. The sensing device of claim 15, wherein the bottom wall defines a second through hole; the second through hole extends through the main body; the at least two connecting pins further comprises a third connecting pin; the extending portion of the third connecting pin extends into the second through hole to the outside of the main body; the signal receiving element is stacked on the bottom wall; the signal receiving element is in direct contact with the end portion of the third connecting pin.

17. A sensing device comprising:
a connecting assembly, the connecting assembly comprising a main body and at least two connecting pins engaged in the main body, the main body defining a receiving groove;
a sensor, the sensor received in the receiving groove and comprising a first electrode layer and a second electrode layer insulated from the first electrode layer, the first electrode layer extending to locate at a same plane with the second electrode layer;
wherein each of the at least two connecting pins is made of electrically conductive material; each of the at least two connecting pins comprises an end portion and an extending portion extending from the end portion; the end portion of each of the at least two connecting pins is engaged in the receiving groove, the extending portion of each of the at least two connecting pins extends through the main body to the outside of the main body; and wherein the first electrode layer is in direct contact with the end portion of one of the at least two connecting pins and the second electrode layer is in direct contact with the end portion of another one of the at least two connecting pins, the sensor is electrically coupled to an external system by the at least two connecting pins, wherein the sensor is a capacitive sensor; the sensor comprises the first electrode layer, the second electrode layer, and an insulating layer between the first electrode layer and the second electrode layer; the insulating layer is elastic.

18. The sensing device of claim 17, wherein the insulating layer comprises a first surface and a second surface; the first surface and the second surface are on opposite sides facing away from each other; the first electrode layer is formed on the first surface and covers the first surface; the first electrode layer extends to partially cover the second surface; the second electrode layer is formed on the second surface and partially covers the second surface.

19. The sensing device of claim 17, wherein the receiving groove comprises at least one side wall and a bottom wall connecting to the at least one side wall; the bottom wall defines two through holes; each of the two through holes extends through the main body; the at least two connecting pins comprises a first connecting pin and a second connecting pin, the extending portion of the first connecting pin or the second connecting pin extends into one of the two through holes to the outside of the main body.

\* \* \* \* \*